United States Patent [19]

Deane

[11] 4,380,025
[45] Apr. 12, 1983

[54] AUXILIARY BLANKING AND AUXILIARY SIMULATED VIDEO LINE GENERATOR UNIT FOR A VIDEO INSPECTION SYSTEM

[75] Inventor: David W. Deane, Otterbein, Ind.

[73] Assignee: Ball Corporation, Muncie, Ind.

[21] Appl. No.: 63,927

[22] Filed: Aug. 6, 1979

[51] Int. Cl.³ .............................................. H04N 7/18
[52] U.S. Cl. .................................... 358/106; 358/183; 356/237
[58] Field of Search ............... 358/106, 126, 165, 105, 358/108, 183; 356/237, 239, 240; 250/223 B, 223 R

[56] References Cited

U.S. PATENT DOCUMENTS

| | | | |
|---|---|---|---|
| 2,798,605 | 7/1957 | Richards | 358/106 |
| 3,257,397 | 6/1966 | Schneider | 358/106 |
| 3,379,329 | 4/1968 | Gambrell et al. | 358/106 |
| 3,624,289 | 11/1971 | Dudley | 358/165 |
| 4,002,823 | 1/1977 | Van Oosterhout | 358/106 |

Primary Examiner—Benedict V. Safourek
Assistant Examiner—Edward L. Coles
Attorney, Agent, or Firm—Gilbert E. Alberding

[57] ABSTRACT

An auxiliary blanking and simulator method and apparatus for providing a blanking window and simulated video pulses for a bright field analyzer video inspection system. Monostables triggered by the horizontal and vertical synchronization pulses of the video inspection system define the horizontal and vertical leading and trailing edges of a blanking window signal. The blanking window signal defines a blanking window within which inspection is inhibited. The blanking window signal is coupled to a reject gate of the video inspection system and to a video monitor for displaying the blanking window. A second group of monostables generates a simulated video signal for enhancing the shoulder blanking capability of the video inspection system. This simulated signal is combined with the video information signal from a video camera before the video signal is electronically processed for defect determination.

19 Claims, 7 Drawing Figures

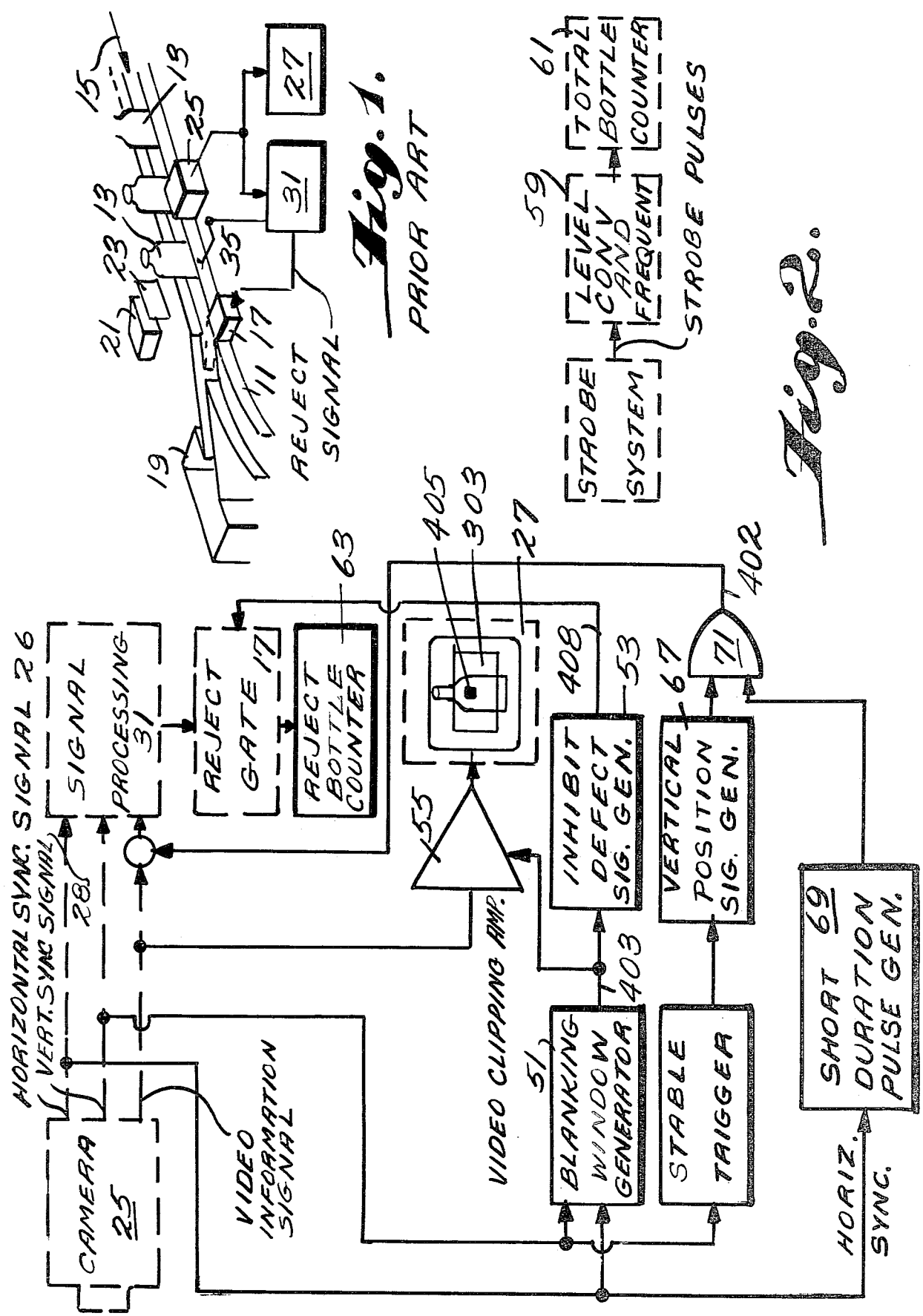

AUXILIARY BLANKING AND AUXILIARY SIMULATED VIDEO LINE GENERATOR UNIT FOR A VIDEO INSPECTION SYSTEM

BACKGROUND OF THE INVENTION

This invention relates in general to methods and apparatus for the video inspection of articles of manufacture. More specifically, this invention relates to video inspection systems and methods wherein an article of manufacture is observed by a video camera as it passes through an illuminated inspection station. Such a system is disclosed in U.S. Pat. No. 4,002,823 issued to Van Oosterhout which teaches a video inspection system for glassware.

In the Van Oosterhout type system, generaly known as a bright field analyzer in the electronic video inspection art, semi-diffused light is directed through a glass bottle to be inspected and is observed by a video camera. The camera produces for each of its scan lines a video signal indicative of the spatial rate of change of the optical refraction characteristic of the scanned portion of the article. Signal processing circuits distinguish between desired refraction characteristics of the article, such as, those produced by lettering, seams, and coloration and undesired refraction characteristics such as those produced by spikes, bird swings and other defects.

Even though the inspection system taught by Van Oosterhout has greatly enhanced the art of bottle inspection, its capabilities are nevertheless limited.

One particular limitation of the Van Oosterhout system is that decorative bottle features often produce, through the signal processing circuits signals, indicia of undesired refraction characteristics causing, rejection of a bottle having no defects. Bright field analyzer video inspection systems utilize an inspection window which defines a region of each bottle to be inspected. Preset inspection criteria are applied throughout this entire region. Therefore, decorative bottle portions within the inspection window may cause an inappropriate rejection. There is no way to inhibit the inspection of smaller regions within the inspection window corresponding to decorative bottle portions.

Another problem involves the scanning of the shoulder region of a bottle. As a video camera scans a bottle under inspection, the scan line crosses the leading edge of the bottle first, it then crosses the body of the bottle, and finally crosses the trailing edge of the bottle. On the shoulder of a bottle, the bottle's leading and trailing edges are particularly thick and tend to "fool" the signal processing circuits into thinking that a defect has been detected. In order to prevent such false defect indications, edge removing circuits, generally referred to as shoulder blanking circuits, are provided to inhibit defect signals generated in response to the scan crossing the leading and trailing edges of the shoulder of a bottle. In essence, shoulder blanking is achieved by generating a horizontal line bar to cover the neck of a bottle. In the case where the entire shoulder of the bottle to be blanked is located within the inspection window, rejection due to apparent defects are inhibited within the shoulder region. However, in the case where the entire container is not viewed by the video camera, it is impossible to provide a continuous shoulder blanking signal. Therefore, the size of the bottle capable of being inspected is limited.

In addition, the bright field analyzer video inspection system in current use does not provide for the automatic counting of the total number of bottles inspected, nor does it provide for the automatic counting of the total number of bottles rejected upon inspection.

SHORT STATEMENT OF THE INVENTION

In order to overcome these limitations in an otherwise useful bright field analyzer video inspection system, the present invention provides an auxiliary blanking unit. It is intended to be an add-on device for use with a bright field analyzer video inspection system of the general type developed by VAn Oosterhout.

The auxiliary blanking unit, according to the present invention, provides a blanking window signal in the form of a simulated horizontal and vertical trigger pulses. This blanking window signal defines a region within the inspection window of a video inspection system within which bottle rejection will be inhibited. By coupling this blanking window signal to the signal processing circuits of a video inspection system, defect signals normally coupled to a reject gate are inhibited with respect to apparent defects detected within the blanking window provided by the present invention. In addition, the blanking window signal can be mixed with a video monitor signal to visually display the blanking window. By adjusting the blanking window to coincide with the decorated region of a bottle under inspection, false defect signals induced by the decoration are inhibited.

The auxiliary blanking unit according to the present invention further provides a shoulder blanking signal. This signal provides simulated trigger pulses which define a line having adjustable position and thickness. This line can be positioned across the shoulder portion of a bottle in order to simulate an upper portion of a bottle outside of the inspection window. In this manner, the signal processing circuits of a video inspection system are "fooled" into reacting as if the entire bottle were within the inspection window.

In addition, the auxiliary blanking unit provides counters for counting the total number of bottles counted and the total number of bottles rejected.

BRIEF DESCRIPTION OF THE DRAWINGS

Other objects, features and advantages of the present invention will become more readily apparent by studying the following detailed description, the appended claims, and the accompanying drawings, wherein:

FIG. 1 is a partial perspective view and partial block diagram of a prior art bright field analyzer video inspection system;

FIG. 2 is a general block diagram of the auxiliary blanking unit according to the present invention;

DETAILED DESCRIPTION OF THE PREFERRED EMBODIMENT

Figure 3:
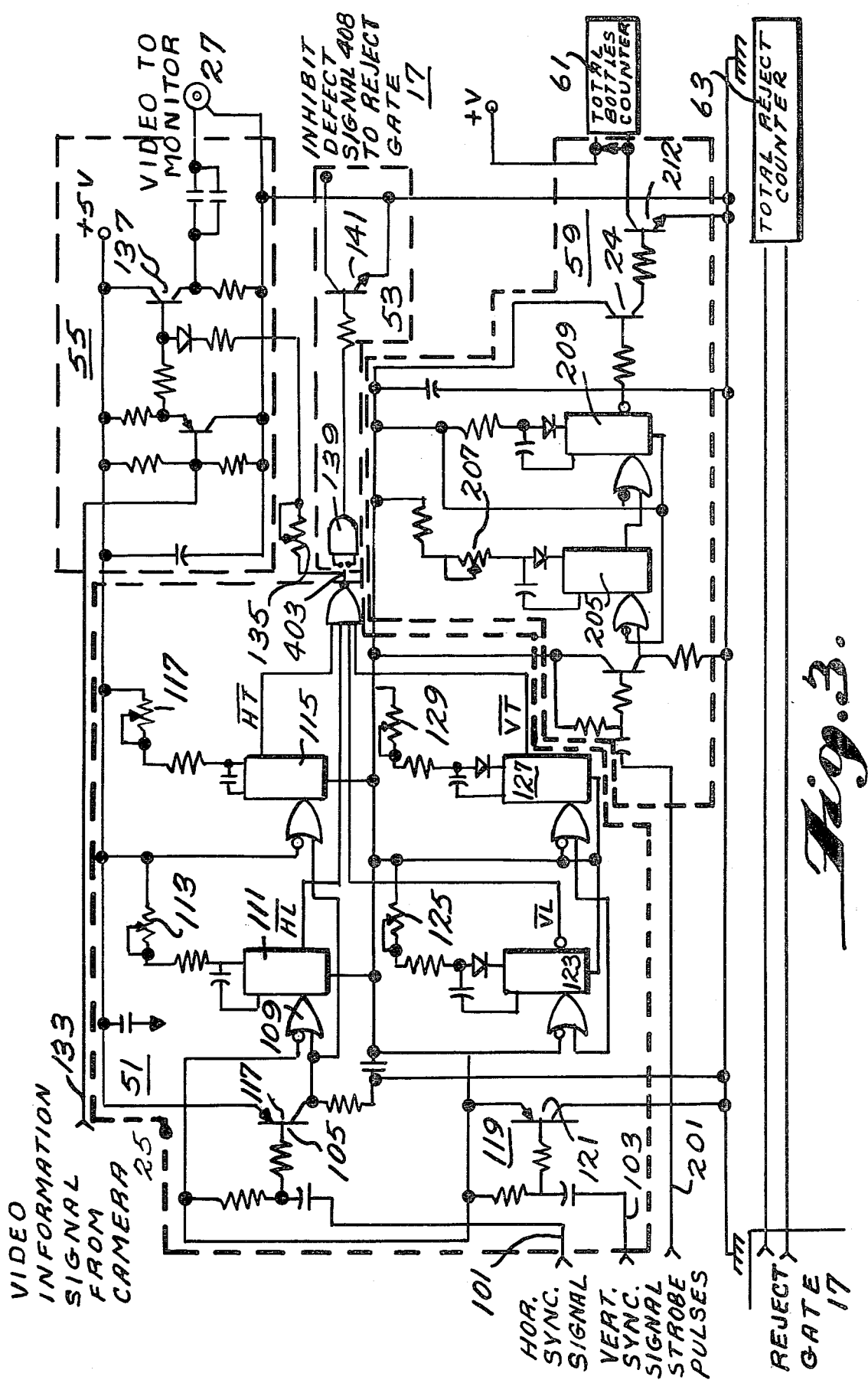
FIG. 3 is a detailed schematic diagram of that portion of the auxiliary blanking unit used for generating the blanking window signal and further includes the total bottle counter and reject bottle counter.

Referring now to the Figures wherein like reference numerals designate like or corresponding parts throughout, and specifically referring to FIG. 1, there is shown a partial perspective view and partial block diagram of a prior art bright field analyzer video inspection system. A conveyor mechanism 11 positioned between various components of an electronic video inspection apparatus transports a train of articles of manufacture, such as bottles 13 in the direction indicated by arrow 15. As each bottle 13 passes through an inspection station, it is inspected for defects or abnormalities, such as, spikes or bird swings. In the event a defective bottle is detected, the electronic video assembly actuates a reject gate 17 positioned downstream of the inspection station for directing the defective bottle away from conveyor mechanism 11 and into a reject platform or container 19.

The inspection assembly includes a semi-diffused light source 21 positioned on one side of and in close proximity to conveyor mechanism 11 for illuminating each of the glass bottles 13 as the bottles pass thereby. A lens 23 is located between light source 21 and the bottle 13 under inspection. A video camera 25 is positioned on the side of conveyor mechanism 11 opposite light source 21 and in alignment therewith for scanning each of the passing illuminated bottles 13 so as to produce a representative standard video signal for coupling to electronic circuits 31 and to a video monitor or display tube 27. Defects occurring within the glass bottles will diffract light passing therethrough to a greater extent than will non-defect regions and as such, defects appear on video monitor 27 as a darkened region. The video signal from camera 25, in addition to being coupled to video monitor 27, is also coupled to signal processor circuits 31 for processing the video signal and isolating portions of the signal indicating defects in a glass bottle 13. Those portions of the video signal indicating the presence of a defect are utilized to generate a reject signal which is applied to reject gate 17 for actuating the reject gate and deflecting a defective bottle onto reject platform 19.

As disclosed in U.S. Pat. No. 3,746,784 issued to Van Oosterhout, in order to overcome distortion due to bottle motion, a strobe mechanism, triggered by a photoelectric detecting device, is utilized in conjunction with light source 21 so as to energize the light source only when a bottle 13 is in the correct position for inspection. Strobe pulses from the strobe mechanism used to indicate that a bottle 13 is in position and light source 21 is energized in response thereto.

As previously discussed, in order to enhance the operating flexibility of a bright field analyzer video inspection system of the type described, an auxiliary blanking unit is provided. As stated, when utilizing the bright field analyzer video inspection system without an auxiliary blanking unit as presently described, it doesn't provide a blanking window within the inspection window and it doesn't provide a continuous shoulder blanking signal when the entire bottle under inspection is not viewed by the video camera.

The auxiliary blanking unit provides a blanking window adjustable to cover decorative regions of the bottles 13 under inspection. During the blanking intervals the operation of signal processing circuit 31 is inhibited. In essence, the blanking window 405 (see FIGS. 2 and 6) is a preset and adjustable region within the inspection window (shown by reference numeral 303 in FIG. 4) within which defects are not observed. The horizontal and vertical starting and stopping positions within the scan of each line in each frame of the video signal are fully adjustable. An inhibit reject signal responsive to this blanking window is coupled to reject valve 17 to inhibit its operation.

The auxiliary blanking unit further provides a shoulder blanking line (shown by reference numeral 401 in FIG. 6) which is generated by a simulated video signal. This simulated signal is a stream of continuous trigger pulses for simulating missing video information necessary for proper shoulder blanking and is hereafter referred to as the shoulder blanking signal 402.

To further enhance the operation of the bright field analyzer video inspection system, there are also provided counters for counting the total number of bottles inspected and total number of bottles rejected.

Referring now to FIG. 2 which is a general block diagram of the auxiliary blanking unit according to the present invention, the general signal flow is detailed. Blocks denoting portions of the prior art bright field analyzer video inspection system are shown with dotted lines to distinguish from the blocks relating to the auxiliary blanking unit. Horizontal and vertical sync signals 26 and 28 respectively from camera 25 are coupled to a blanking window generator 51. Blanking window generator 51 generates a blanking window signal 403 defining blanking window 405 (see FIG. 6) within which inspection is to be inhibited. The size and position of this window can be adjusted to coincide with the decorative region 407 of a bottle 13. Blanking window signal 403 is coupled to an inhibit defect signal generator 53 for generating an inhibit defect signal for coupling to reject gate 17. In addition, blanking window signal 403 is coupled to a video clipping amplifier 55 interposed between camera 25 and video monitor 27. In this manner, blanking window 405 defined by the blanking window signal appears as a dark region on the monitor as shown pictorially in block 27.

Provisions are made for the counting of the total number of bottles inspected and the total number of bottles rejected. Strobe pulses for triggering light source 21 are coupled to a level conversion and frequency limiting circuit 59. Level conversion and frequency limiting circuit 59 is in turn is coupled to a counter 61 for displaying the total number of bottles inspected. The reject signal is coupled to a second counter 63 for displaying the total number of bottles rejected.

Shoulder blanking line 401 (shown in FIG. 6) is separately generated. Vertical sync signal 28 from camera 25 is coupled to a stable trigger 65 for producing pulses in synchronism with the vertical sync signal. The output of stable trigger 65 is coupled to a vertical position signal generator 67. Horizontal sync signal 26 from camera 25 is coupled to a short duration pulse generator 69 for generating short duration pulses in synchronism with the horizontal sync signal. The pulses from short duration pulse generator 69 and vertical position signal generator 67 are logically combined by a gate 71 to form a simulated video signal 402 defining shoulder blanking line 401 for mixing with the video information signal from camera 25 prior to its coupling to signal processor 31.

Referring now to FIG. 3 there is shown a detailed schematic diagram of that portion of the auxiliary blanking unit for generating the blanking window 405 and further including the counters. Blanking window generator 51 is shown having inputs 101 and 103 for horizontal sync 26 and vertical sync 28 signals respectively from camera 25.

The horizontal sync signals provide timing reference for horizontal lead and trail signals. Horizontal sync signal 26 is coupled to a buffer amplifier 105 including transistor 107 along with its associated components and gate 109. Buffer amplifier 105 converts horizontal sync signal 26 to a TTL compatible level.

The TTL converted horizontal sync signal is then coupled to a monostable 111 having an astable period controllable by variable resistor 113 and other monostable related components. The output of monostable 111 at its pin 9 forms a horizontal lead signal designated $\overline{HL}$. In a similar fashion, the TTL converted horizontal sync signal is also coupled to a second monostable 115 having an astable period controlled by variable resistor 117 and the other monostable related components. Monostable 115 generates a horizontal trail signal designated $\overline{HT}$.

Similarly, the vertical sync signals provide timing reference for vertical lead and trail signals. Vertical sync signal 28 is coupled to a buffer amplifier 119 including a transistor 121 and its related components. Buffer amplifier 119 converts vertical sync signal 28 to a TTL compatible signal. The TTL converted vertical sync signal is coupled to a monostable 123 having an astable period adjustable by variable resistor 125 and the other monostable related components. The output monostable 123 defines a vertical lead signal designated $\overline{VL}$. In a similar fashion, the TTL converted vertical sync signal is coupled to a monostable 127 having an astable period controllable by variable registor 129 and the other related monostable components. The output of monostable 127 defines a vertical trail signal designated $\overline{VT}$.

The horizontal lead, horizontal trail, vertical lead, and vertical trail signals $\overline{HL}$, $\overline{HT}$, $\overline{VL}$ and $\overline{VT}$ are combined by a logic gate 131 to form blanking window signal 403 at the output of this gate. Monostable 111, 115, 123, and 127 generate portions of the blanking window signal, each timed in relation to horizontal and vertical sync signals 26 and 28. Blanking window signal 403 at the output of gate 131 is utilized to generate the inhibit defect signal 408 for coupling to reject gate 17.

Blanking window signal 403 is also coupled to video clamping amplifier 55 so as to mix with the video information signal from camera 25 and induce the appropriate display on monitor 27. Video clipping amplifier 55 includes an input 133 carrying the video information signal from camera 25. The blanking window signal at the output of gate 131 is coupled as a clipping signal through variable resistor 135 to clipping amplifier 55. Within clipping amplifier 55, and specifically at the base of transistor 137, blanking window signal 403 is combined with the video information signal from camera 25 to form a composite signal at the output of transistor 137 for coupling to video monitor 27. When combined in this manner with the video information signal from camera 25, blanking window signal 403 will cause a darkened region to appear on monitor 27 corresponding to the blanking window 405 selected by the operation of variable resistors 113, 117, 125 and 129. The position and size of blanking window 405 as depicted in the monitor image shown in FIG. 2 is defined by the timing of the horizontal lead and trail and vertical lead and trail signals with respect to the timing of the pulses of horizontal sync signal 26 and vertical sync signal 28.

Blanking window signal 403 at the output of gate 131 is also coupled to a gate 139 which in turn is coupled to a transistor switch 141 for generating inhibit defect signal 408 for coupling to reject gate 17. Inhibit defect signal 408 is generated by virtue of the clamping of any positive defect signals to ground through transistor switch 141.

Continuing to refer to FIG. 3, there is also schematically detailed level conversion and frequency limiting circuit 59 having an input 201 coupled to a source of strobe pulses. These pulses are synchronized with the energizing of light source 21 for the inspection of each of bottles 13. Strobe pulses are coupled to a transistor 203 for converting these pulses to a compatible five-volt pulses for the triggering of a monostable. The output of transistor 203 is coupled to a monostable 205 having a period controllable by variable resistor 207. The purpose of monostable 205 is to prevent bottle counting above a predetermined rate adjusted by resistor 207. This rate is chosen such that only inspection strobe pulses will be counted. A monostable 209 provides a sufficient length pulse to trigger total bottle counter 61 by means of driver transistors 211 and 212. Also shown in FIG. 3 is total reject counter 63 coupled to reject gate 17.

Figure 4:
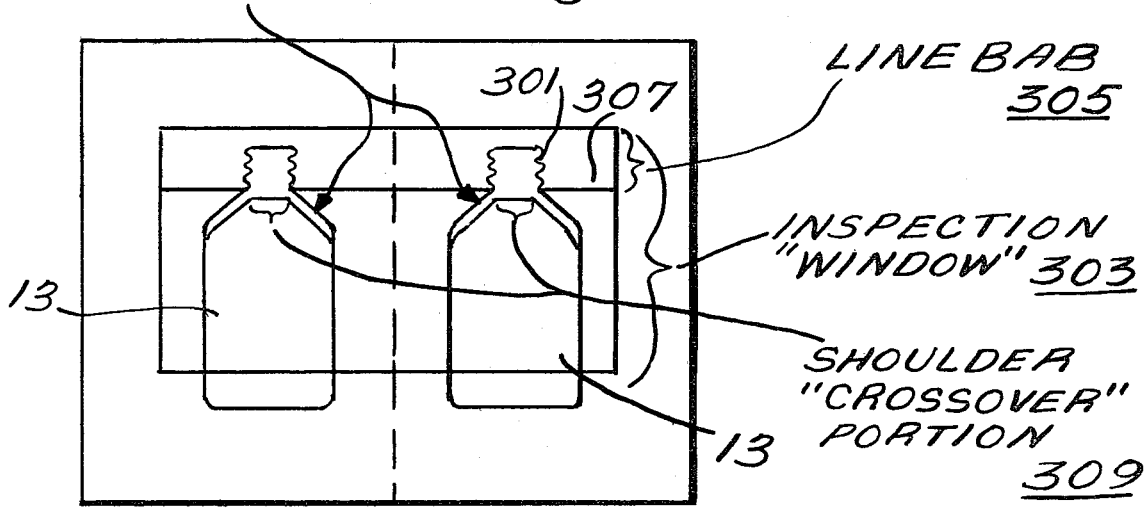
FIG. 4 is an illustration of a representative video monitor display of the shoulder blanking line bar generated by the prior art bright field analyzer video inspection system in the case where bottles being inspected fit within the inspection window.

Referring now to FIG. 4 there is shown a diagram of a typical monitor display showing the shoulder blanking line bar 305 used with bottles 13 fitting within inspection window 303. Two bottles 13 are shown because in the prior art video inspection system two bottles are monitored simultaneously and this a typical arrangement.

The normal shoulder blanking mode of the prior art bright field analyzer video inspection system requires that the entire upper portion 301 of a bottle 13 be contained within inspection window 303. Shoulder blanking will then occur at the first detection of the bottle located below line blanking bar 305 and the maximum height to which shoulder blanking will occur is determined by the position below line bar 305. Shoulder blanking begins below line bar 305 and the portion of the shoulder detected within the line bar is inhibited until the shoulder falls below this line.

It should be noted that shoulder blanking may occur only if the bottle is detected within or outside of the line bar 305 but entirely within inspection window 303. The horizontal or crossover portion 309 of the shoulder blanking covers the crown and shoulder of a bottle 13 located within line bar 305 but delayed until the finish of a line.

Figure 5:
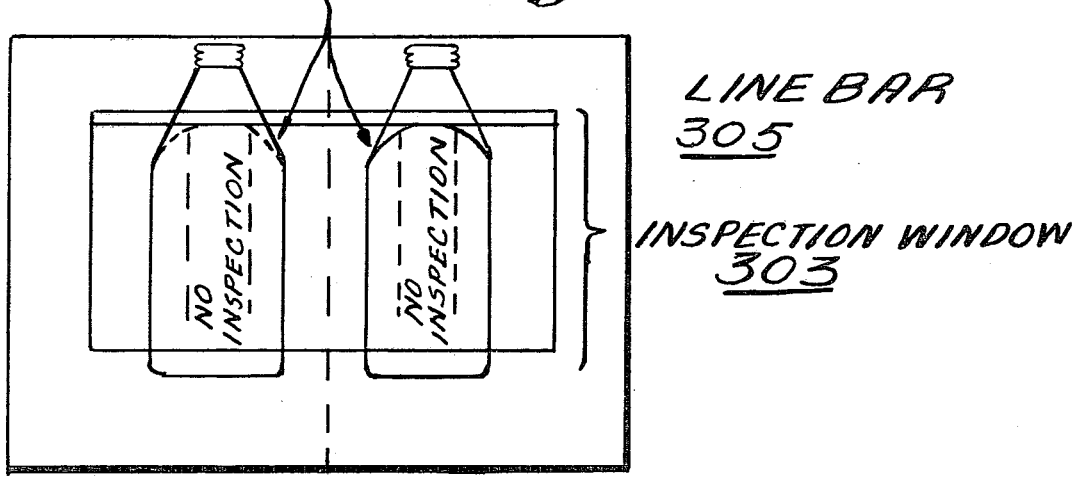
FIG. 5 is an illustration of a representative video monitor display of the shoulder blanking line bar generated by the prior art bright field analyzer video inspection system in the case where tall bottles do not fit within the inspection window.

Referring now to FIG. 5 which is a typical monitor view of tall bottles, no shoulder blanking would occur in the region below the portion of the bottle outside of the inspection window 303. Since inspection begins below shoulder blanking line bar 305, there would be no inspection in the center portion of the bottle.

To overcome this limitation with tall bottles and in other circumstances wherein the top of a bottle 13 may not be viewed, shoulder blanking line 401 is generated by shoulder blanking signal 402 (see FIG. 6) which is a simulated video signal within inspection window 303. Shoulder blanking signal 402 corresponds to the missing portion of bottle 13 outside inspection window 303. The optimum form for this artificial signal is a line drawn above the missing portion of shoulder and below the top of inspection window 303.

Figure 6:
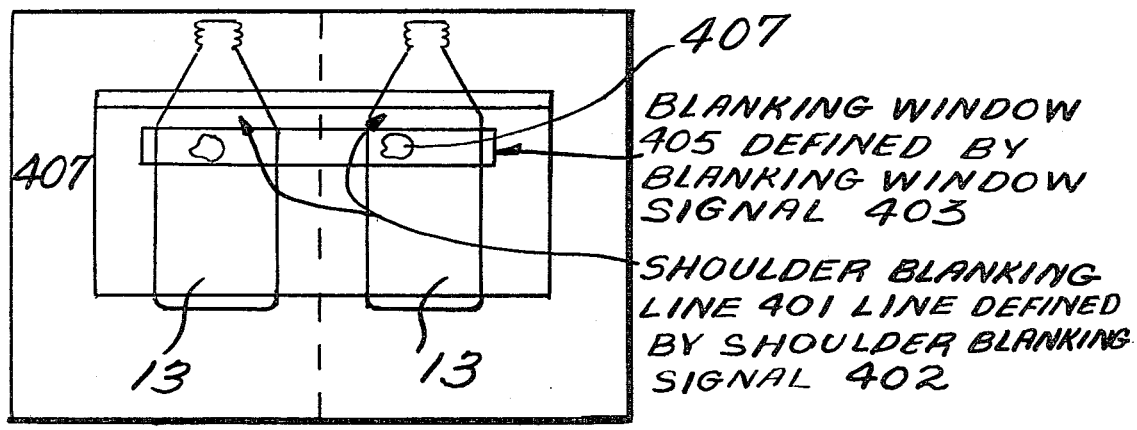
FIG. 6 is an illustration of a representative video monitor display showing a blanking window and shoulder blanking line generated by the auxiliary blanking unit according to the present invention.

Referring now to FIG. 6, there is shown a typical monitor view when the auxiliary blanking unit according to the present invention is operating. Shoulder blanking signal 402 defines shoulder blanking line 401. The height of both lines 401 as shown in the Figure are the same so that only one vertical adjustment control is provided. The right and left hand ends of each line are positioned above the missing blanking by use of the position controls and the width of the lines is adjusted using the respective width controls. Also shown in this figure is blanking window 405 defined by the blanking window signal 403 as used to cover decorated regions 407 of bottles 13.

A similar arrangement may be used to inspect pinched waste or "May West" containers. For that type of bottle, the shoulder blanking line 401 is placed within the narrowest portion of the container and the top of inspection window 303 is placed just above the shoulder blanking line with line bar 305 extending just below the shoulder blanking line.

Figure 7:
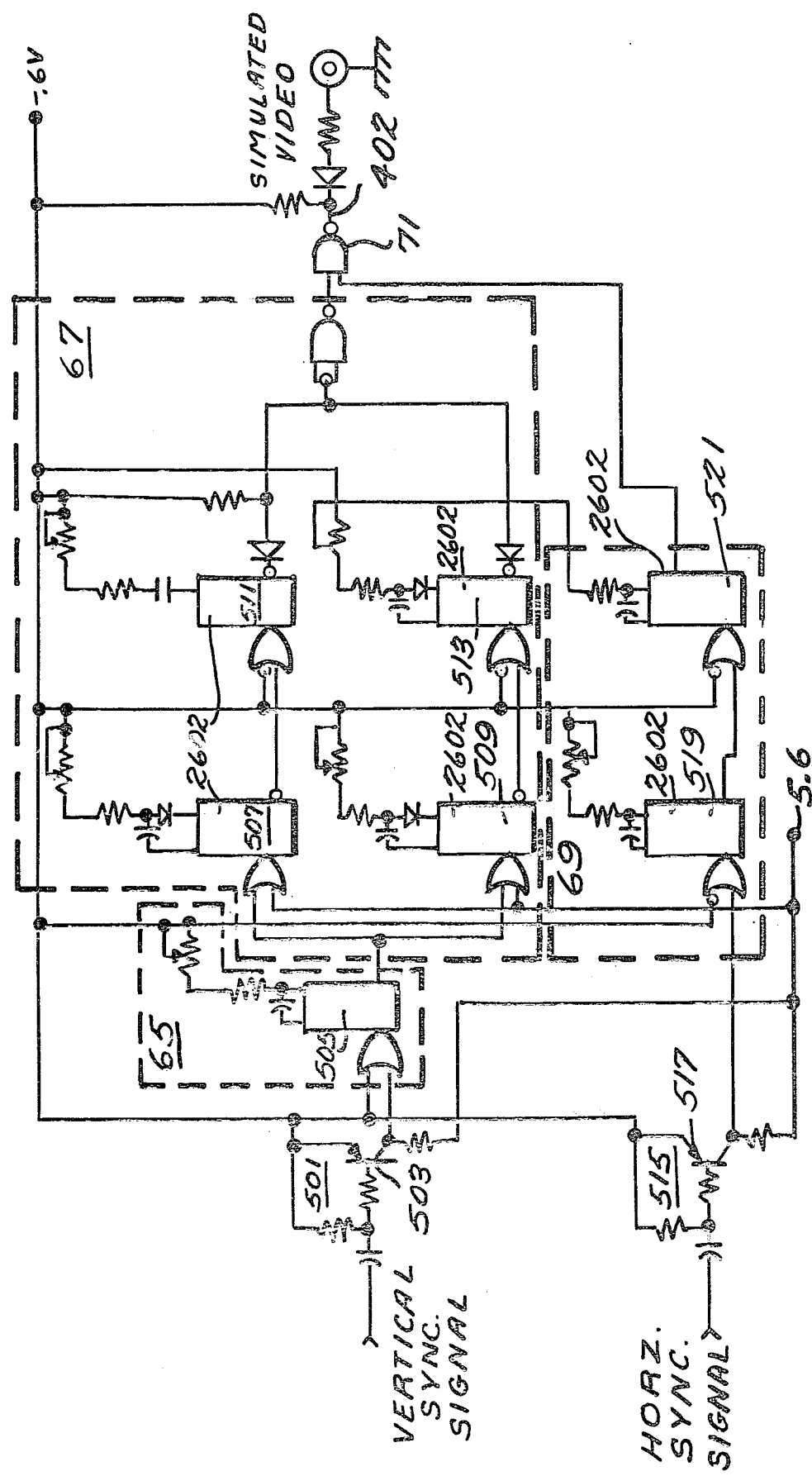
FIG. 7 is a detailed schematic diagram of that portion of the auxiliary blanking unit for generating the shoulder blanking line.

Referring now to FIG. 7 there is shown a schematic diagram of the circuitry for generating shoulder blanking signal 402. This schematic includes stable trigger 65, vertical position generator 67, short duration pulse generator 69 and gate 71 as shown in the general block diagram of FIG. 2.

Vertical sync signal 28 is coupled to a buffer amplifier 501 including a transistor 503 and its associated circuitry. Amplifier 501 converts vertical sync signal 28 to a 0 −5 volt pulses. The output of amplifier 501 is coupled to stable trigger 65 including a monostable 505 and its associated components. The output of stable trigger 65 is coupled to vertical position signal generator 67 including monostables 507, 509, 511 and 513. Monostables 507 and 509 are used to determine the vertical position of each simulated line and monostables 511 and 513 determine the width of each line. The vertical signals generated by vertical position signal generator 67 are limited to a small portion of each horizontal line by being summed with a short duration pulse from short duration pulse generator 69.

Horizontal sync signal 26 is coupled to a buffer amplifier 515 including transistor 517 and its associated components. Amplifier 515 converts horizontal sync signal 26 into a 0- −5 volt signal. The output of amplifier 515 is coupled to short duration pulse generator 69 including monostables 519 and 521. Monostable 519 determines the vertical position and monostable 512 actually generates the short duration pulse. It should be noted that the astable period of each monostable is controlled by a variable resistor in combination with a fixed resistor and capacitor. Thus, the timing of each monostable may be determined by the formula $$T \approx 0.3\, RC \left(1 + \frac{0.7}{R}\right)$$

where R is in kilohms, c is in picofarads (pf) and T is in nanoseconds (ns). The short duration pulses from short duration pulse generator 69 are coupled with the signal from vertical position signal generator 67 by gate 71, producing the simulator video signal for mixing with the video information signal from camera 25.

In essence, the system shown in general block diagram in FIG. 2 and schematically in FIGS. 3 and 7, incorporates a new method for enhancing the flexibility of a bright field analyzer video inspection system.

In order to inhibit inspection of a smaller region within a large inspection window 303 so as to prevent the automatic rejection of inspected bottles 13 having decorated regions 407, an artificial blanking window 405 is generated to inhibit inspection in a predetermined region. This blanking window 405, having edges related to the timing of horizontal and vertical sync signals 26 and 28, is generated by artifical trigger pulses mixed with the video information signal from camera 25. The signal 403 defining the blanking window is utilized to generate an inhibit defect signal 408 which is then logically combined with the reject signal from the video inspection system. In this manner apparent defects within the blanking window do not automatically cause reject sorting to occur.

To obtain added flexibility with regard to shoulder blanking, particularly for tall bottles and pinched waste bottles, a simulated line is drawn having a position adjustable with respect to the inspection window. This line drawn by a shoulder blanking signal is mixed with the video information signal from camera 25.

Therefore it is apparent that there has been provided an apparatus and method for generating a blanking window for inhibiting the automatic rejection of an inspective article of manufacture by video inspection system. There has further been provided an apparatus and method for developing simulated video signals to enhance the automatic blanking capability of a video inspection system.

Other embodiments and modification of the present invention will be apparent to those of ordinary skill in the art having the benefit of the teaching presented in the foregoing description and drawings. It is therefore, to be understood that the invention is not to be unduly limited and such modifications are intended to be included within the scope of the appended claims.

What is claimed and is desired to be secured by Letters Patent of the United States is:

1. In a video inspection system for the inspection of articles of manufacture including a video camera for supplying a video information signal and utilizing horizontal and vertical sync signals, a blanking apparatus for producing within a predetermined inspection window a blanking window within which inspection is inhibited, said blanking apparatus comprising:

means for generating a horizontal lead signal having timing adjustable with respect to said horizontal sync pulses;

means for generating a horizontal trail signal having timing adjustable with respect to said horizontal sync pulses;

means for generating a vertical lead signal having timing adjustable with respect to said vertical sync pulses;

means for generating a vertical trail signal having timing adjustable with respect to said vertical sync pulses; and means for combining said horizontal lead signal, horizontal trail signal, vertical lead signal and vertical trail signal to form a blanking window signal defining said blanking window within which inspection is inhibited.

2. A blanking apparatus according to claim 1 further including:
means for generating in response to said blanking window signal an inhibit defect signal for inhibiting the rejection of inspected articles of manufacture for defects observed within said blanking window.

3. A blanking apparatus according to claim 1 wherein said video inspection system further includes a video monitor for displaying said video information signal from said video camera and wherein said blanking apparatus further includes:
means for combining said blanking window signal with said video information signal for producing a video monitor signal for driving said video monitor thereby visually displaying said blanking window within said predetermined inspection window.

4. A blanking apparatus according to any one of claims 1, 2 or 3 wherein said means for generating said horizontal lead signal includes a monostable having an adjustable astable period and triggered by said horizontal sync pulses.

5. A blanking apparatus according to any one of claims 1, 2 or 3 wherein said means for generating said horizontal trail signal includes a monostable having an adjustable astable period and triggered by said horizontal sync pulses.

6. A blanking apparatus according to any one of claims 1, 2 or 3 wherein said means for generating said vertical lead signal includes a monstable having an adjustable astable period and triggered by said vertical sync pulses.

7. A blanking apparatus according to any one of claims 1, 2 or 3 wherein said means for generating said vertical trail signal includes a monostable having an adjustable astable period and triggered by said vertical sync pulses.

8. In a video inspection system for the inspection of articles of manufacture including a video camera for supplying a video information signal and utilizing horizontal and vertical sync signals, a blanking apparatus for producing within a predetermined inspection window a blanking window within which inspection is inhibited comprising:
a first monostable having an adjustable astable period for coupling to and triggering by said horizontal sync signal, the output of said first monostable defining a horizontal lead signal;
a second monostable having an adjustable astable period for coupling to and triggering by said horizontal sync signal, the output of said second monostable defining a horizontal trail signal;
a third monostable having an adjustable astable period for coupling to and triggering by said vertical sync signal, the output of said third monostable defining a vertical lead signal;
a fourth monostable having an adjustable astable period for coupling to and for triggering by said vertical sync signal, the output of said fourth monostable defining a vertical trail signal; and
a gate for combining said horizontal lead, horizontal trail, vertical lead, and vertical trail signals to produce a blanking window signal, which in combination with said horizontal and vertical sync signals defines a blanking window.

9. A blanking apparatus according to claim 8 further comprising:
a video amplifier for combining said video information signal with said blanking window signal for producing a monitor signal for displaying said blanking window.

10. In a video inspection system for the automatic inspection of articles of manufacture including a video camera for supplying a video information signal, a signal processor, a reject gate coupled to said signal processor, and utilizing horizontal and vertical sync pulses, a method for inhibiting inspection within a predetermined blanking window comprising the steps of:
generating a horizontal lead signal bearing a first predetermined timing relationship to said horizontal sync pulses;
generating a horizontal trail signal bearing a second predetermined timing relationship to said horizontal sync pulses;
generating a vertical lead signal bearing a third predetermined timing relationship to said vertical sync pulses;
generating a vertical trail signal bearing a fourth predetermined timing relationship to said vertical sync pulses;
combining said horizontal lead, horizontal trail, vertical lead and vertical trail, signals to form a blanking window signal defining said predetermined blanking window within which inspection is inhibited.

11. A method for inhibiting inspection according to claim 10 further including the step of:
coupling said blanking window signal to said reject gate so as to prevent activation thereof during inspection of the region defined by said blanking window.

12. A method for inhibiting inspection according to claim 11 further including the step of:
combining said blanking window signal with said video information signal for display on a video monitor whereby said blanking window defined by said blanking window signal is visually displayed.

13. In a video inspection system for the automatic inspection of articles of manufacture including a video camera for supplying a video information signal which is electronically processed for determining defects in said articles of manufacture, said system utilizing horizontal and vertical sync pulses, a shoulder blanking apparatus for generating a shoulder blanking signal adjustable with respect to said horizontal and vertical sync signals comprising:
means for generating a vertical position signal having timing adjustable with respect to said vertical sync pulses;
means for generating a horizontal position signal having timing related to said horizontal sync pulses;
means for combining said vertical position signal and said horizontal signal to form said shoulder blanking signal; and
means for combining said shoulder blanking signal with said video information signal prior to the electronic processing of said video information signal for the determination of defects.

14. Apparatus according to claim 13 wherein said means for generating said vertical position signal includes:
at least one monostable having an adjustable astable period and triggered by said vertical sync signal.

15. Apparatus according to claims 13 or 14 wherein said means for generating said horizontal position signal includes:
   a monostable having an adjustable period and triggered by said horizontal sync signal.

16. An auxiliary blanking apparatus for use with a bright field analyzer video inspection system wherein said bright field analyzer video inspection system includes a video camera, for scanning articles of manufacture and generating a video information signal including defect information, a signal processor for processing the video signal within a predetermined inspection window and a reject gate activated by the signal processor for rejecting articles determined by the signal processor to have a defect, said auxiliary blanking apparatus comprising in combination:
   means for generating a blanking window signal defining a blanking window within said predetermined inspection window said blanking window defining a region within which inspection is inhibited;
   means for generating an inhibit defect signal responsive to said blanking window signal for coupling to and inhibiting said reject gate;
   means for generating a shoulder blanking video signal in synchronism with said horizontal and vertical sync signals; and
   means for combining said simulated video signal with said video information signal prior to the coupling of said video signal to said signal processor.

17. An auxiliary blanking unit according to claim 16 further including means for combining said blanking window signal with said video information signal to form a monitor signal for visually displaying said blanking window.

18. An auxiliary blanking apparatus for use with a bright field analyzer video inspection system wherein said bright field analyzer video inspection system includes a strobe system for lighting articles of manufacture to be inspected, a video camera for scanning said articles and generating a video information signal including defect information within a predetermined inspection window, a signal processor for processing said video information according to predetermined criteria, and a reject gate actuate in response to said signal processor, said auxiliary blanking unit comprising:
   means for generating a blanking window signal defining a blanking window within said inspection window, said blanking window, defining a region within which inspection is inhibited;
   means for inhibiting said reject gate for video information signals corresponding to said blanking window;
   means for generating a shoulder blanking signal for combining with said video information signal;
   a counter coupled to said strobe system for counting the number of articles inspected;
   a second counter coupled to said reject gate for counting the number of articles rejected.

19. In a video inspection system including a video camera for scanning articles of manufacture along successive video scan lines in a scanning raster, and a signal processor for processing video signals generated by said camera within an inspection window, a method for modifying the video signals related to an edge or shoulder region of an article comprising:
   generating a simulated video signal corresponding to at least one line having a predetermined length less than a complete video scan line but extending substantially across a scanned article at a location within said inspection window and having a predetermined width; and
   mixing said simulated video signal with said video signal prior to the processing of said video signal by said signal processor whereby the processor is caused to treat said simulated video signal line as a terminating edge of said article.

* * * * *